United States Patent [19]

Redey et al.

[11] Patent Number: 4,814,062

[45] Date of Patent: Mar. 21, 1989

[54] MEMBRANE REFERENCE ELECTRODE

[75] Inventors: Laszlo Redey, Downers Grove; Ira D. Bloom, Bolingbrook, both of Ill.

[73] Assignee: The United States of America as represented by the United States Department of Energy, Washington, D.C.

[21] Appl. No.: 147,825

[22] Filed: Jan. 25, 1988

[51] Int. Cl.$^4$ ............................................. G01N 27/36
[52] U.S. Cl. ................................... 204/420; 204/1 T; 204/413; 204/422; 204/423; 204/435
[58] Field of Search ............... 204/435, 420, 1 A, 422, 204/423, 413

[56] References Cited

U.S. PATENT DOCUMENTS

| | | | |
|---|---|---|---|
| 3,483,111 | 12/1969 | Zaromb | 204/1 T X |
| 4,166,009 | 8/1979 | Fray | 204/1 T |
| 4,414,093 | 11/1983 | Redey et al. | 204/412 |
| 4,465,744 | 8/1984 | Susman et al. | 429/191 |
| 4,477,403 | 10/1984 | Pust | 264/104 |
| 4,544,614 | 10/1985 | Kucera et al. | 429/193 |

OTHER PUBLICATIONS

B. V. Joglekar et al, Canadian Metallurgical Quaterly, vol. 12, No. 2, pp. 155-158 (1973).
Limin Hsueh et al., J. Electrochem. Soc., vol. 118, No. 7, pp. 1128-1130, (1971).
Bockris et al., "An All-Glass Reference Electrode for Molten Salt Systems", Journal of Scientific Instruments, Nov. 1956.
Kucera et al., "Ionic Conductivities and Glass Transition Temperatures of $Na_2O-ZrO_2-Al_2O_3-SiO_2$ Glasses", Journal of the Electrochemical Society: Electrochemical Science and Technology, Oct. 1986.
New Technology from DOE, Argonne National Laboratory, Press release, Aug. 26, 1987.
Redey et al., "Glass-Membrane Reference Electrodes for Sodium- and Sulfur-Activity Measurements", The Electrochemical Society Symposium, May 1987.
Bloom et al., "Sodium- and Sulfur-Activity Measurements Using Glass-Membrane Reference Electrodes/Sensors", The Electrochemical Society Meeting, Oct. 1987.

Primary Examiner—G. L. Kaplan
Attorney, Agent, or Firm—Hugh W. Glenn; Robert J. Fisher; Judson R. Hightower

[57] ABSTRACT

A reference electrode utilizes a small thin, flat membrane of a highly conductive glass placed on a small diameter insulator tube having a reference material inside in contact with an internal voltage lead. When the sensor is placed in a non-aqueous ionic electrolytic solution, the concentration difference across the glass membrane generates a low voltage signal in precise relationship to the concentration of the species to be measured with high spatial resolution.

14 Claims, 2 Drawing Sheets

MEMBRANE REFERENCE ELECTRODE

CONTRACTUAL ORIGIN OF THE INVENTION

The U.S. Government has rights in this invention pursuant to contract number W-31-109-ENG-38 between the U.S. Department of Energy and Argonne National Laboratory.

BACKGROUND OF THE INVENTION

This invention relates to electrodes and more particularly to membrane reference electrodes for use in analyzing specific ion concentrations in batteries and other ionic solutions.

In the development of a high temperature nonaqueous energy cell, it is important that the concentration gradients of the cell be known. One manner of analyzing for concentration and other electrolyte properties is to generate a known reference electrode potential with an electrical double layer in the reference electrode, thereby measuring the potential difference between the reference electrode and the electrode of interest. Electrolytic solutions of some battery cells can have cell operating temperatures of between 100° and 600° C. At a cell operating temperature of about 400° C., temperature variatons across a cell on the order of about 50° C. have been detected; electrolyte concentrations also vary within a cell; such variations cause the EMF of the half cell to vary considerably within the confines of the cell. The change of voltage, if undetected, prevents an effective determination of cell voltages under the various conditions of cell operations. For example, temperature effects may cause the cell voltage to change by values in the order of at least 12 mV; it becomes important to detect changes in the cell voltage along the orders of 3 to 4 mV with an accuracy of about 1 mV. In addition, the concentration ingredients of the various components in the electrolytic solution can vary significantly throughout the cell volume, causing similar variations in EMF across the cell. It becomes very important in the analysis of the efficiency and operation of a battery cell to measure and calculate the potential of the electrolytic solution at various precise points within the cell in order to develop a working knowledge of the cell and cell efficiency.

Previous reference electrodes and other membrane sensors have been characterized by elongated tubes of ceramic or similar material with a spherical membrane having an area of one square centimeter or more forming the tip. In general the membrane material has been of low conductivity; the relatively large area of the membrane contacting the solution resulted in a low spatial resolution of potential and activity gradient in the electrolytic solution.

SUMMARY OF THE INVENTION

Accordingly an object of the subject invention is a reference electrode having a membrane of a highly conductive material and capable of stable EMF measurements at a wide temperature range.

A further object of the subject invention is a multifunctional reference electrode comprising an insulating metal oxide tube holding a reference material and an ion diffusion barrier associated with the tube in contact with an electrolytic solution for measuring chemical, electrochemical, thermal, or mechanical properties of the electrolytic solution.

Another object of the subject invention, is a reference electrode system utilizing a thin, flat membrane of highly conductive glass and presenting a relatively small surface area to the electrolytic solution for precise positioning of the electrode within the electrolytic system.

These and other objects are realized by the subject invention wherein there is provided a reference electrode having a small, thin membrane of a highly conductive material formed as a flat disk extending across the tubular end of an electrode housing. The disk has a minimum surface area of approximately 0.5 to 7 mm$^2$, with a thickness of about 1 mm. The small electrochemically active area of the reference electrode makes precise positioning possible in an electrochemical system of interest. Once a reference material is sealed within the electrode assembly the small flat disk area acts electrochemically like a Luggin capillary tip; however, instead of diffusion or convection mixing of the system components with the reference material both inside and outside the electrode, as may occur in a Luggin capillary tip, the reference electrode of the subject invention chemically isolates the reference electrolyte from the rest of the system. The disk preferably is formed of a sodium-ion-conducting glass of a certain composition which permits stable EMF measurements to reflect the activity or concentrations of specific elements in the electrolytic system. Within the range of the glass components which are useful in the subject invention, the composition can be modified for compatibility with the chemistry associated with a particular system without changing the resistivity of the glass to any great degree.

DETAILED DESCRIPTION OF THE DRAWINGS

Figure 1:
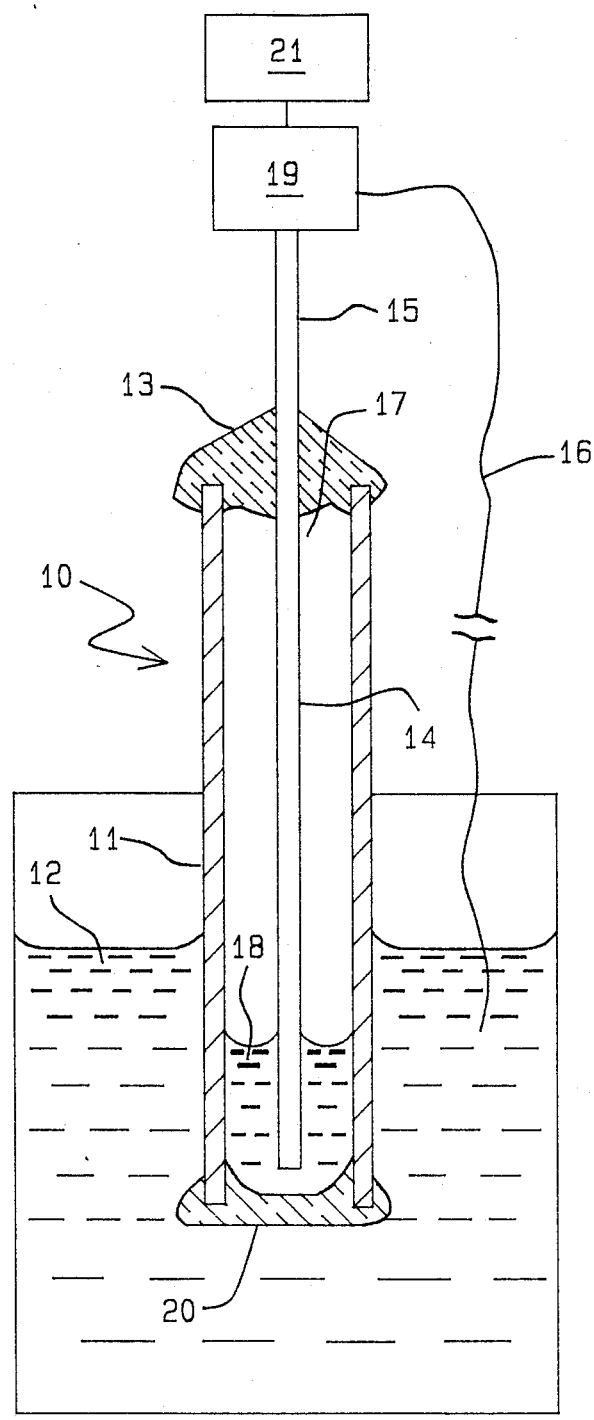
FIG. 1 is a schematic of the reference electrode of the subject invention.

Referring now to FIG. 1 there is shown the reference electrode 10 of the subject invention including an elongated tubular housing or body 11 formed of an electrically insulating metal oxide material, such as alumina ($\alpha$-Al$_2$O$_3$). The material of the electrode body may vary according to the properties of the electrolytic solution 12 being measured and thereby provide compatibility with the solution as appropriate. In a typical electrolytic solution 12 which may be measured, alumina may be used for its compatibility with the system being measured, i.e., a Na/S cell environment, such as a Na$_2$S$_4$ melt. The alumina electrode body is sealed at the top such as by glass 13, formed of a Pyrex ™ or other suitable high temperature resistant glass substance. An internal voltage lead 14 comprising a molybdenum wire (0.2 mm) is utilized when using sodium as a reference material. The internal voltage lead may be of other elemental composition as appropriate when using other reference materials as known in the art. For instance, when used with an NaCl/AlCl$_3$ melt, the internal voltage lead would be aluminum. The external portion 15 of the internal voltage lead is connected to an apparatus for reading out the EMF impedance and may be monitored, for example, on a strip chart recorder indicated generally at 21 through a high input impedance ($10^{14}$), 1:1 operational amplifier 19.

External lead 16 connects the monitoring apparatus 19 with the electrolytic solution 12.

A reference material 18 is used which would vary dependent on the material being measured, and may constitute a material such as Na, a sodium alloy, or $Na_2S_x$. The material 18 is placed or electrolyzed into the electrode body 11 which is sealed at an upper end. As stated above, the upper seal can be as shown in FIG. 1 as a glass seal 13, or should the system require, the seal might be a stainless steel Swagelok ™ cap having a soft aluminum ferrule, or a TEFLON sealing member.

Membrane 20 at the lower end of the electrode body 11 is of a sodium ion-conductive material. Preferably a glass is selected but a ceramic, such as $\beta'$-alumina, $\beta''$-alumina, and NASICON also are contemplated. A glass membrane 20 may be prepared and placed on the lower end of the electrode body 11 in the following manner. The molten glass is prepared by a solid state reaction of $Na_2CO_3$, $Al_2O_3$, $ZrO_2$, and $SiO_2$ at 875° C. followed by melting of the resulting white solid at 1700° C. Preferably the glass melt and the membrane fashions therefrom have the composition of 30–45% $Na_2O$, 1–17% $Al_2O_3$, 0–13% $ZrO_2$, and 25–69% $SiO_2$. Membranes may be fabricated from this glass stock by pulling thin rods from the melt with a stainless steel tube having a 0.95 cm OD and 30–40 cm long. The thin rods are annealed in a furnace well of a helium atmosphere glove box at approximately 450° C. for 10–16 hours. A gas-oxygen flame is used to attach a thin, flat membrane 20 of the ion-conducting glass prepared above to an end of a high density electrically insulating metal oxide tube formed of a material resistant to corrosion in the electrolytic solution being tested. More specifically, the glass rod is melted onto the heated end of the tube to form the flat membrane. In a $Na_2S_x$ or polysulfide melt, $\alpha$-$Al_2O_3$ (Alumina) has been found preferable as the material for the tube. The alumina tube is preferably approximately 3 mm in outside diameter with an inside diameter of from 1.0 to nearly 3.0 mm. The membrane thus exposed to external influences is a flat surface of approximately 0.5 $mm^2$ to 7 $mm^2$, preferably 1 to 3 $mm^2$. In use the external voltage lead 16 is a molybdenum wire of approximately 0.5 mm diameter. Together the sealed electrode assembly 10 and the external molybdenum wire 16 are immersed in the melt at 300°–400° C. and allowed to thermally equilibrate. The membrane-sealed electrode 10 is directed to the specific position for which readings are desired and the EMF is monitored on the recorder 19.

The following examples further illustrate the present invention.

EXAMPLE 1

A reference electrode assembled and formed by reacting $Na_2CO_3$, $Al_2O_3$, $ZrO_2$, and $SiO_2$ at 875° C. The resulting white solid is melted at 1700° C., and the glass rods are pulled and are annealed at 450° C. for 16 hours, and are used to form a flat membrane on the open end of an alumina tube having an outside diameter of about 3.0 mm. The reference material of sodium is electrolyzed with small dc currents into the interior of the electrode after the membrane is placed on the electrode tip. The electrode was tested in a $Na_2S_4$ melt to determine the EMF stability and thermal coefficient of the EMF in the range of approximately 300°–400° C. The agreement of the measured EMFs with previously measured thermodynamic values was assessed. The stability of the electrode in agreement with previously measured thermodynamic values were good over the course of 99 hours at 350° C.

EXAMPLE 2

Figure 2:
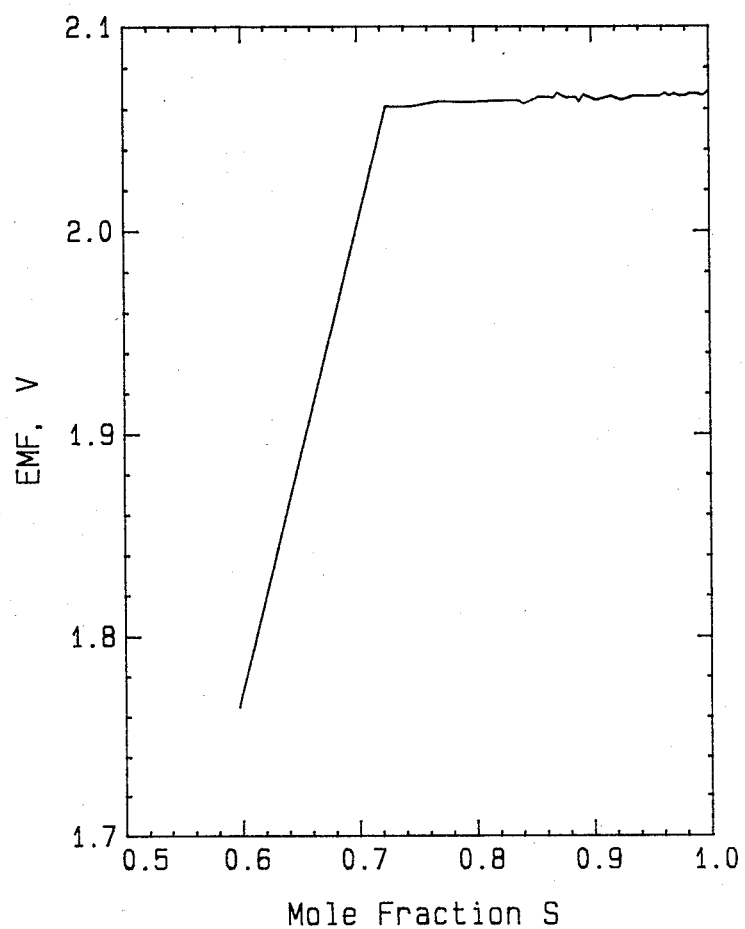
FIG. 2 is a graph of a coulometric titration showing EMF vs. S mole fraction.

A reference electrode was constructed and assembled as set forth in example 1. In the interior of the electrode was placed sulfur. This electrode was tested in liquid sodium at about 320° C. Coulometric titrations in the Na|S cell were performed using the electrode, with about 2 mAh capacity in 16.67 $\mu$Ah steps. A typical coulometric titration curve is given in FIG. 2. The curve shows a broad plateau down to about 71 mol % S, as expected. Immediately following the plateau is a linear region from 71 mol % to 60 mol % S (2.06 V to 1.77 V). These titrations show the transformation from a phase-separated material to a single phase.

EXAMPLE 3

Reference electrodes were assembled and formed as set forth in example 1 but with the exception of having a reference material of sodium polysulfide. The electrode of the subject invention was tested in sodium polysulfide melts to determine EMF stability, reproducibility and dependence on sodium activity difference in a given system. Several reference electrodes of identical construction and content were placed in a common sodium polysulfide melt. In systems such as $Na_2S_x$/$Na_2S_y$ (x, y = 3, 4, 5) at 309° C. after thermal equilibration, the EMF measurements were reproducible to +/−1 mV and were stable (+/−1-2 mV) for at least 18 hours. This data is set forth in table I.

TABLE I

| Results of Reproducibility Experiments at 309° C. | |
|---|---|
| System | EMF, mV |
| $Na_2S_5$\|$Na_2S_4$ | 125 |
|  | 124 |
| $Na_2S_5$\|$Na_2S_3$ | 291 |
|  | 292 |
|  | 293 |
| $Na_2S_4$\|$Na_2S_3$ | 170 |
|  | 171 |
| $Na_2S_4$\|$Na_2S_4$ | 0 |
|  | 0 |

The use of the small thin, flat membrane having an active area of minimal dimensions, the membrane comprising sodium-ion-conducting glass yields stable, reproducible EMF measurements which can reflect specific ion activity or concentration differences within an electrolytic system at a wide range of temperatures, such as between 20° C.–600° C. with no decrease in accuracy. Thus, uses from metal and electrolyte melts to room temperature battery analysis is possible, as well as a wide range of other electrochemical analyses. The small electrochemically active area of the membrane allows greater spatial resolution of the activity gradients in a given electrode non-aqueous ionic solutionl. In addition, because the reference electrode of the subject invention chemically isolates the reference material from the electrolytic solution being tested through use of the thin, flat glass membrane, the electrode has a longer life with greater spatial resolution and reproducible results throughout its life.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

We claim:

1. A reference electrode comprising a housing, a seal on an upper end of said housing and an interior voltage lead comprising an electrically conductive wire extending from outside said housing through said seal into the housing interior, an internal reference material within said housing, said internal lead selected from the group consisting of aluminum wire and a molybdenum wire and extending at least partially into and contacting said reference material, said housing having a lower opening, an ion-conductive membrane sealing said lower opening and having an external flat surface, whereby said reference electrode when placed in contact with a non-aqueous ionic solution in combination with an external voltage lead may measure the EMF between said voltage leads of said non-aqueous ionic solution with increased spatial resolution with respect to said external voltage lead.

2. The reference electrode of claim 1 wherein said housing comprises an electrically insulating metal oxide.

3. The reference electrode of claim 1 wherein said membrane is formed of a sodium-ion-conducting glass.

4. The reference electrode of claim 3 wherein said glass membrane has a composition of 30–45% $Na_2O$, 1–17% of $Al_2O_3$, 0–13% of $ZrO_2$ and 35–69% $SiO_2$.

5. The reference electrode of claim 1 wherein said external flat surface is from about 1 to 3 $mm^2$.

6. The reference electrode of claim 1 wherein said non-aqueous ionic solution comprises a molten salt.

7. A reference electrode comprising a housing, said housing having a seal at an upper end, a voltage lead selected from the group consisting of aluminum wire and molybdenum wire and extending through said seal into said housing, a reference material in the interior of said housing, said voltage lead being at least partially immersed and contacting said material, and an ionically conductive glass membrane sealing the lower end of said housng, said glass membrane having the composition of 30–45% $Na_2O$, 1–17% $Al_2O_3$, 0–13% $ZrO_2$ and 25–69% $SiO_2$.

8. The reference electrode of claim 7 wherein said chemically resistant housing is formed of $Al_2O_3$.

9. The reference electrode of claim 7 wherein said glass membrane has an external surface area of about 3 $mm^2$.

10. The reference electrode of claim 7 wherein said glass membrane has an external flat surface.

11. A reference electrode comprising an electrically insulated housing, a seal on an upper end of said housing and an internal voltage lead selected from the group consisting of aluminum wire and molybdenum wire extending from outside said housing through said seal into the housing interior, an internal reference material within said housing selected from the group consisting of sodium, sodium alloys and polysulfides, said internal lead contacting said reference material, said housing having a lower opening, said lower opening, a conductive glass membrane formed of a mixture of $Na_2O$, $Al_2O_3$, $ZrO_2$, and $SiO_2$ sealing said lower opening and having an external flat surface of from about 0.5 $mm^2$ to amount 7 $mm^2$, whereby said reference electrode when placed in contact with a non-aqueous ionic solution in combination with an external voltage lead may measure the EMF of said non-aqueous ionic solution with increased spatial resolution.

12. The reference electrode of claim 11 wherein said housing comprises an alumina material.

13. The reference electrode of claim 11 wherein said conductive glass membrane is formed from a glass melt having a composition of 30–45% $Na_2O$, 1–17% of $Al_2O_3$, 0–13% of $ZrO_2$, and 25–69% $SiO_2$.

14. The reference electrode of claim 11 wherein said glass membrane has a flat external surface of about 3 $mm^2$.

* * * * *